United States Patent [19]

Venbrux

[11] Patent Number: 5,443,497
[45] Date of Patent: Aug. 22, 1995

[54] PERCUTANEOUS PROSTHETIC BY-PASS GRAFT AND METHOD OF USE

[75] Inventor: Anthony Venbrux, Baltimore, Md.

[73] Assignee: The Johns Hopkins University, Baltimore, Md.

[21] Appl. No.: 155,641

[22] Filed: Nov. 22, 1993

[51] Int. Cl.⁶ .................................................. A61F 2/06
[52] U.S. Cl. ........................................... 623/1; 623/12; 604/8; 606/151; 606/191
[58] Field of Search ............... 623/1, 3, 12; 604/8; 606/151, 153, 191

[56] References Cited

U.S. PATENT DOCUMENTS

| 2,935,068 | 5/1960 | Donaldson | 604/8 |
| 3,042,021 | 7/1962 | Read | 604/8 |
| 4,230,119 | 10/1980 | Blum | 604/8 |
| 4,503,568 | 3/1985 | Madras . | |
| 4,617,932 | 10/1986 | Kornberg . | |
| 4,776,337 | 10/1988 | Palmaz . | |
| 4,850,960 | 7/1989 | Grayzel . | |
| 4,957,508 | 9/1990 | Kaneko et al. | 623/1 |
| 4,994,071 | 2/1991 | MacGregor . | |
| 5,007,926 | 4/1991 | Derbyshire | 606/191 |
| 5,104,399 | 3/1992 | Lazarus | 623/1 |
| 5,330,782 | 7/1994 | Kanazawa | 623/1 |
| 5,360,443 | 11/1994 | Barone et al. | 623/12 |

FOREIGN PATENT DOCUMENTS 2105197  3/1983  United Kingdom ............ 623/12

Primary Examiner—Paul Prebilic
Attorney, Agent, or Firm—Cushman, Darby & Cushman

[57] ABSTRACT

A generally tubular prosthetic device is provided which includes a first stent having a central axis and a flow passage defined therethrough and being sized for insertion into a target lumen. A first, proximal member extends from a sidewall of proximal stent and is in fluid communication with the flow passage. A second, distal stent is provided having central axis and a flow passage defined therethrough and being sized for insertion into the target lumen. A second, distal member extends from a sidewall of the distal stent and is in fluid communication with the flow passage of the distal stent. The prosthetic device also includes a generally tubular central member that interconnects and fluidly couples the first and second stents via the proximal and distal members. A method of employing the device is also disclosed.

22 Claims, 3 Drawing Sheets

PERCUTANEOUS PROSTHETIC BY-PASS GRAFT AND METHOD OF USE

BACKGROUND OF THE INVENTION

This invention relates to a prosthetic device, and more particularly, to a prosthetic arterial bypass, venous bypass or arterial-venous graft.

When an artery or vein becomes occluded, a surgical procedure is typically performed by a vascular surgeon to restore proper blood flow. The known procedure includes a formal surgical incision and exposure of the blocked artery or vein. A prosthetic bypass member or a natural vein is then sutured to the blocked vessel both upstream and downstream of the occlusion so as to divert the flow of blood around the blockage.

A similar surgical procedure is required to place a graft between an artery and a vein, which is clinically used in dialysis patients. Such formal surgical procedures require the use of an operating room and, as a result, are costly.

SUMMARY OF THE INVENTION

It is an object of the present invention to provide a non-surgical prosthetic device and method for either bypassing an occlusion in a lumen or for connecting two lumens, which eliminates the need for a formal surgical procedure.

In accordance with the principles of the present invention, this objective is obtained by providing a generally tubular prosthetic device which includes first and second terminal stents. As used herein, the term "prosthetic device" includes a device having natural or synthetic materials, or a combination thereof. The first stent, also referred to herein as the proximal stent, has a central axis and a flow passage defined therethrough and is sized for insertion into a first portion of a first target lumen. A first, proximal member extends from a sidewall of the proximal stent and is in fluid communication with the flow passage. The proximal member is preferably inclined with respect to the central axis of the proximal stent.

The second terminal stent, also referred to herein as the distal stent, has a central axis and a flow passage defined therethrough and is sized for insertion into a second portion of the first target lumen or a second target lumen. A second, distal member extends from a sidewall of the distal stent and is in fluid communication with the flow passage of the distal stent. The distal member is preferably inclined with respect to the central axis of the distal stent.

The prosthetic device also includes a generally tubular central member that interconnects and fluidly couples the first and second terminal stents via the proximal and distal members.

In accordance with another aspect of the present invention, a method of installing a device within an occluded lumen so as to bypass the occlusion, or as a graft between two lumens, is provided.

The method includes the steps of making a puncture through a first portion of a first lumen at one stent entry site; inserting a distal stent of the prosthetic device in a collapsed state through the puncture into the first lumen; permitting the distal stent to expand so as to engage the interior wall of the first lumen; permitting a portion of the distal stent to extend through the puncture; making a puncture through a second portion of the first lumen or in a second lumen at another stent entry site; inserting a proximal stent of the prosthetic device in a collapsed state through the puncture into the second portion of the first lumen or into the second lumen; permitting the proximal stent to expand so as to engage the interior wall of the first or second lumen; permitting a portion of the proximal stent to extend through the puncture; and disposing a central member in the skin and fascia between the entry sites so as to fluidly couple the proximal and distal stents within subcutaneous tissue and fascia so that fluid may flow through the proximal stent, through the central member and through the distal stent so as to either bypass an occlusion or graft two lumens.

Other objects, features and characteristics of the present invention, as well as methods of operation and functions of related elements of the structure, and the combination of the parts and economics of manufacture, will become more apparent upon consideration of the detailed description and appended claims with reference to the accompanying drawings, all of which form a part of the specification.

DETAILED DESCRIPTION OF THE PRESENTLY PREFERRED EXEMPLARY EMBODIMENT

Figure 1:
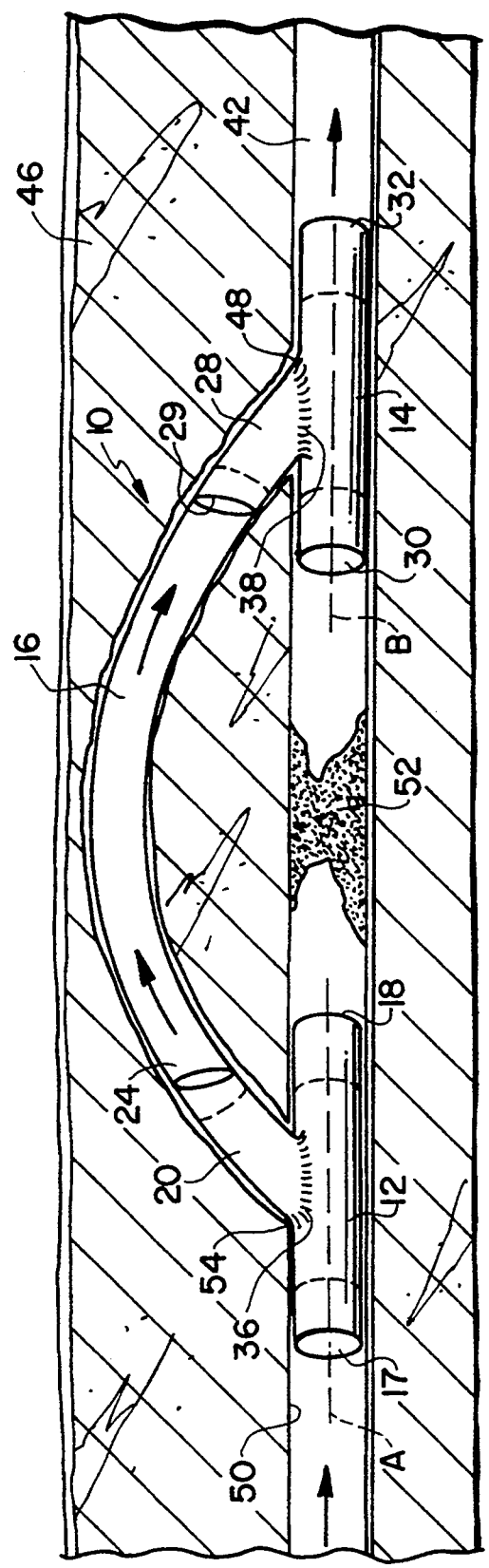
FIG. 1 is a schematic illustration of a prosthetic device provided in accordance with the principles of the present invention, shown installed in an occluded lumen.

A device, generally indicated at 10, is shown for bypassing an occluded lumen or for coupling two lumens. Although the device may be employed as either a bypass device or as a graft, the device 10 will be described herein with reference to bypassing an occluded lumen.

The device 10 includes a proximal stent 12 for placement upstream of the occlusion and a distal stent 14 for placement downstream of the occlusion. A central member 16 fluidly couples the proximal and distal stents. As shown, the proximal and distal stents are disposed within the lumen, while the central member is disposed within the skin and fascial layer, bypassing the occlusion.

The proximal stent 12 is generally tubular and has an inlet 17 and an outlet 18. Furthermore, the proximal stent 12 is preferably a collapsible and expandable stent having a flow passage defined therethrough. In the illustrated embodiment, the proximal stent is an expandable metal mesh stent, however, it can be appreciated that a non-metallic stent may also be employed. Stents that are expandable upon temperature changes or stents that have "memory" properties may also be used. The proximal stent 12 includes a tubular proximal member 20 coupled to and extending from a side thereof so as to be in fluid communication with the flow passage. The proximal member may be made integral with the proximal stent 12, if desired. The proximal member 20 is preferably inclined with respect to the central axis A of the proximal stent 12. The proximal member 20 has an outlet 24 defined at an end thereof. Thus, the proximal stent 12 and the proximal member 20 cooperate to define a generally "Y" shaped juncture, so as to minimize turbulence of fluid flowing therethrough.

The device 10 also includes a generally tubular distal stent 14 which is similar to the proximal stent 12. Thus, the distal stent 14 is preferably a collapsible and expandable stent having a flow passage defined therethrough. Like the proximal stent, the distal stent 14 is preferably an expandable metal mesh stent. Again, it can be appreciated that a non-metallic stent may be employed. The distal stent 14 is open at both ends 30 and 32. The distal stent 14 includes a tubular distal member 28 coupled to and extending from a side thereof so as to be in fluid communication with the flow passage of the distal stent. The distal member 28 may be made integral with the distal stent 14, if desired. The distal member 28 is preferably inclined with respect to the central axis B of the distal stent 14, toward the proximal member 20, the function of which will become apparent below. Thus, the distal stent 14 and the distal member 28 cooperate to define a generally "Y" shaped juncture, which reduces turbulence of fluid flowing therethrough. The distal member 28 is open at outlet 29. Outlet 29 of the distal member 28 is directed generally toward outlet 24 of the proximal member 20, the function of which will became apparent below.

As stated above, the device 10 includes the generally tubular central member 16 disposed between and coupled to the distal and proximal members. The central member is preferably composed of PTFE (polytetrafluoroethylene) material or equivalent Food and Drug Administration approved material. In the illustrated embodiment, ends 36 and 38 are flared and disposed over the proximal and distal members 20 and 28 respectively. When the device 10 is installed to bypass the blockage or to create a communication between an artery and a vein, the flared ends 36 and 38 extend into the lumen through the puncture so as to seal the puncture. As an alternative to providing the flared ends, ends of the central member may simply be attached to the proximal and distal members and, preferably, a coating is provided on the proximal and distal members, extending onto the surface of the proximal and distal stents to provide a seal.

It can be appreciated that ends 36 and 38 may be attached to the proximal and distal tubular members in any known manner as necessary or desirable. In the illustrated embodiment, the ends 36 and 38 are hooded over the tubular members. Thus, the ends 36 and 38 may then be sewn or adhered by adhesive to the tubular members to ensure a robust connection. Alternatively, portions of the stents and tubular members may be covered with PTFE material or other coating, as indicated by the dashed lines in FIG. 1. The central member can then be sewn or adhered to the covered portions. Thus, in the illustrated embodiment, the tubular members are inclined in a direction toward one another, with the central member disposed therebetween, so as to facilitate fluid flow therethrough. It may be appreciated, however, that the tubular members may be disposed substantially perpendicular to the central axes of the tubular members, if the grafting or bypass procedure so requires.

The central member 16 may be made available in a variety of lengths, one of which may be selected for the procedure in question. Alternatively, the central member 16 may have an accordion-type configuration so that the length thereof may be adjusted.

Figure 3:
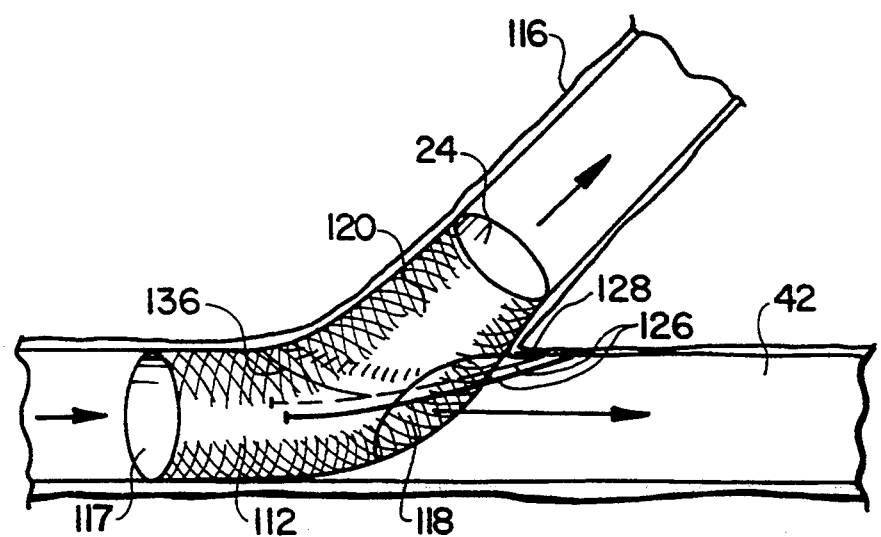
FIG. 3 is a schematic illustration of another embodiment of the prosthetic device showing one end thereof installed in a lumen.

FIG. 3 shows a portion of another embodiment of the prosthetic device 10 of the invention. Only the proximal stent 112 of the prosthetic device is shown, however, it can be appreciated that the distal stent is of similar construction. The central member 116 is identical to that shown in FIG. 1. The proximal stent 112 is substantially similar to the proximal stent 12 of FIG. 1. However, instead of permitting the tubular proximal stent 112 to extend beyond the proximal member 120, the proximal stent 112 terminates at a location where it is coupled to the proximal member 120, as shown if FIG. 3. In the illustrated embodiment, the proximal stent 112 includes an inlet 117 and an outlet 118. Thus, blood flowing in the lumen is directed through the proximal stent 112 from inlet 117 through outlet 118 and also through the proximal member 120, as shown by the arrows in FIG. 3. It can be appreciated, however, that the outlet 118 need not be provided in the stent 112 and blood passing through the lumen may pass directly through the mesh stent 112. Since the proximal stent 112 does not extend downstream of the proximal member 120, retention braces 126 are preferably provided to enhance the stability of the device. One end of each retention brace 126 is coupled to the proximal stent 112 at opposing side surfaces thereof. The other ends of the retention braces 126 extend downstream of the proximal member 120 and, when disposed in the lumen, contact the upper wall of the lumen to provide additional support to the device. Further, the proximal member 120 may include a lip 128 which engages the upper wall of the lumen to further enhance stability of the device 10 within the lumen. Thus, the "Y" configuration is maintained.

Figure 2:
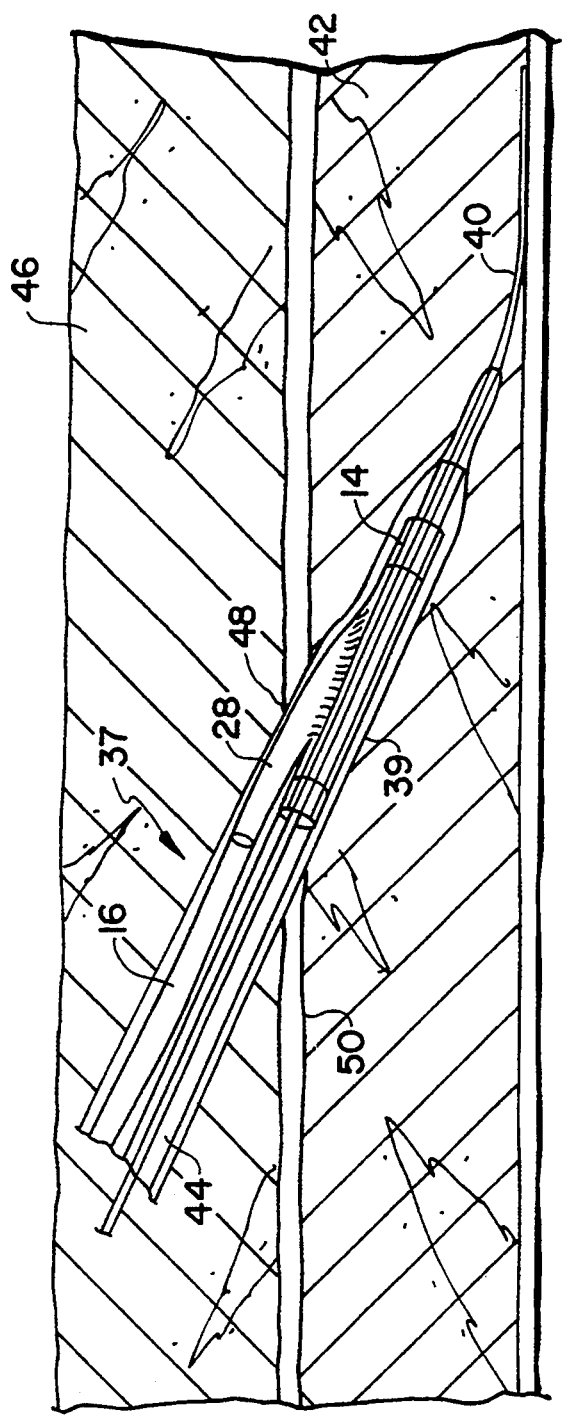
FIG. 2 is a schematic illustration of a delivery device shown delivering one end of the prosthetic device into the lumen.

The installation of the device 10 will be appreciated with reference to FIGS. 1 and 2. A delivery device 37 for delivering the device 10 to the lumen is shown in FIG. 2. As shown, the device 37 includes an elongated hollow member 39 which is large enough to house therein a stent and the central member in an adjacent relation. A guide wire 40 is disposed within a guide wire channel extending axially through the device 37 and is used for guiding the device 37 into the lumen 42. Alternatively, it can be appreciated that the guide wire may be disposed through the central member 16, through member 20 or 28 and into the lumen so as to guide the device into the lumen. Stent 12 or 14 is disposed within the device 37 in a collapsed condition with the central member 16 coupled thereto. The guide wire 40 extends through the stent. A pusher member 44 is disposed behind the stent so as to remove the stent from the device 37.

A preferred method of installing the device 10 to bypass an occlusion is as follows. An small incision or puncture is made in the skin and fascial layer 46 approximately midway between the area to be bypassed and at area where the bypass will terminate. The delivery device 37 containing the central member and one of the stents connected to the central member is inserted through the midway incision and tunneled either proximally or distally of the blockage toward a predetermined stent entry site. A small puncture 48 is made through the lumen or vessel wall 50 near one stent entry site. When the bypass requires a device 10 short in length, the delivery device 37 is simply turned downward and inserted into the puncture 48 in the lumen. If the puncture 48 is made downstream of the blockage, the guide wire is used to guide the device into the lumen with the distal stent 14 being inserted into the lumen in a collapsed state through the downstream puncture 48. Pusher member 44 is pushed forward so as to extract the distal stent 14 from the delivery device 37. The distal stent 14 then self-expands so as to engage the interior wall of the lumen. The device 37 may be slid over the central member and moved out from either the midway incision or the incision in the skin and fascial layer near the stent entry site, leaving the stent in the lumen, with the central member coupled thereto. Instead of sliding the device 37 so as to remove it from the stent and central member, the device may include longitudinal slits therein. The slits permit the device to be peeled away from the central member and then removed. Upon removal of the device 37, the distal member 28 is disposed so as to extend through the downstream puncture.

If a bypass of significant length is required, for example a bypass from the groin to an area below the knee, several small incisions may be made in the skin and fascial layer to assist in the tunnelling of the central member. Thus, the delivery device 37 can be inserted into the midway incision and tunneled, then drawn out of another incision located along the path of tunneling, then reinserted into that incision, until the delivery device 37 and central member are tunneled toward the incision in the skin and fascial layer at one end of the bypass region. The delivery device 37 is then drawn out of the incision in the skin and fascial layer and then reinserted thereinto at an appropriate angle so as to access the lumen which may be disposed deeply within the fascial layer. The stent 14 is then inserted into the lumen through the puncture 48 as explained above, and the delivery device 37 is removed from the incision in the skin and fascial layer near the stent entry site.

The procedure is repeated at the other side of the blockage 52. Thus, the proximal stent is coupled to the other end of the central member and the proximal stent and central member are placed into the delivery device 37. The delivery device 37 is then inserted into the midway incision and tunnelled toward the other stent entry site. A second puncture 54 is made in the lumen at the other stent entry site. The proximal stent 12 is inserted into the lumen via the delivery device 37 in a collapsed state through the puncture 54. The proximal stent is then ejected from the delivery device and the delivery device 37 is then peeled away from the central member and removed, leaving the proximal member 20 extending through the puncture 54. The delivery device is then withdrawn from the midway or incision in the skin and fascial layer near the stent entry site leaving the central member 16 disposed between the proximal and distal members. As explained above, when a bypass of significant length is required, several small incisions may be made in the skin and fascial layer to assist in the tunnelling of the central member. Further, the delivery device 37 may need to be removed from the incision in the skin and fascial layer near the stent entry site and be reoriented and reinserted at the appropriate angle so as to access the lumen.

Thus, as shown in FIG. 1, the proximal and distal stents are disposed within the lumen and the proximal, central and distal members are disposed within the skin and fascial layer to bypass the blockage 52. As shown by the arrows in FIG. 1, blood may flow into the proximal stent, through the central member, and out through the distal stent. Thus, a lengthy and deep incision at either end of the bypass is eliminated due to the tunnelling procedure and the percutaneous placement of the stents.

The size of the expanded stents 12, 20 and/or 14 and 28 are matched to the size of the vessel based on an earlier performed diagnostic arteriogram or diagnostic venogram.

It can be appreciated that the order of placing of the stents depends on the particular application. Thus, it may be preferable to place the proximal stent first within the lumen and then, thereafter, place the distal stent within the lumen.

The device 10 can be used to bypass an arterial blockage and a venous blockage and is also applicable to create an artery to vein graft. It can be appreciated that the installation procedure outlined above may be employed to graft two different lumens. Thus, instead of making two punctures in the same lumen, one puncture is made in each of the two lumens to be connected. The proximal stent 12 is installed in one lumen and the distal stent 14 is installed in the other lumen, with the central member 16 providing communication between the two lumens. Thus, when functioning as an artery-vein graft, the device 10 communicates between an artery and a vein rather than between separate regions of the same artery or the same vein.

Arterial bypass grafts, venous bypass grafts, or artery-venous grafts are traditionally performed in an operating room by a surgeon skilled in vascular procedures. However, the percutaneous graft or bypass device 10 does not require formal surgical procedures and lengthy incisions and may be placed non-surgically, enabling the procedure to be performed under local anesthesia in, for example, a radiology department. Sutures are not required to couple the device to the lumen, but may be employed if desired. Since the sizes of the distal and the proximal tubular stents are preferably preselected based on lumen size, proper fit within the lumen is generally realized upon expansion thereof.

It is within the contemplation of the invention that the distal and proximal stents may be joined with a vein (natural material) instead of using the central member, composed of synthetic material. Thus, for example, a saphenous vein can be harvested from the patient and used in place of the central member, with the distal and proximal stents acting as the anchors for the bypass or graft. The use of a vein would be desirable when a long bypass is required, for example, a bypass from the groin to the calf or ankle. The use of a vein with the proximal and distal stents would be performed in an operating room by a vascular surgeon utilizing the above-mentioned procedure. Further, the procedure makes the surgeon's job easier since placement difficulty and the degree of dissection is minimized. Another advantage of using the proximal and distal stents with the vein is that the incisions in the region to be bypassed are kept small.

It can be seen that the device of the present invention provides an effective means of bypassing a blockage within arteries or veins and/or providing communication between an artery and a vein. The provision of the proximal and distal members extending from the puncture sites ensures that a non-surgical procedure may be employed when using a central member of prosthetic material, since sutures are not required. Further, the proximal and distal stents may be used with natural material when longer bypasses are required.

While the invention has been described in connection with what is presently considered to be the most practical and preferred embodiment, it is understood that the invention is not limited to the disclosed embodiment but, on the contrary, is intended to cover various modifications and equivalent arrangements included within the spirit and scope of the appended claims.

What is claimed is:

1. A prosthetic device comprising:
 a generally tubular proximal stent having a central axis and a flow passage defined therethrough and being sized for insertion into a target lumen, said proximal stent including a proximal member extending from a sidewall thereof so as to be in flow communication with said flow passage;
 a generally tubular distal stent having a central axis and a flow passage defined therethrough and being sized for insertion into a target lumen, said distal stent including a distal member extending from a sidewall thereof so as to be in flow communication with the flow passage of the distal stent; and
 a generally tubular central member having first and second ends and extending between the said proximal member and said distal member and being in flow communication therewith so as to provide flow communication between said proximal and said distal stents,
 said proximal and distal stents being constructed collapsible expandable and are and arranged so as to engage walls of the target lumen.

2. The device as defined in claim 1, wherein each of said proximal and distal members extend from said proximal and distal stents to define a generally "Y" juncture.

3. The device as defined in claim 1, wherein each of said proximal and distal stents comprise metal mesh, said first and second ends of said central member being hooded over said proximal member and said distal member, respectively, in such a manner to provide substantially sealed flow communication between said proximal and said distal stents.

4. The device as defined in claim 1, wherein the central member is composed of polytetrafluoroethylene.

5. The device as defined in claim 3, wherein said first and second ends of the central member are sewn to said proximal and distal members respectively.

6. The device as defined in claim 3, wherein said first and second ends of the central member are attached by adhesive to said proximal and distal members respectively.

7. The device as defined in claim 3, wherein the ends of the central member are flared.

8. The device as defined in claim 3, wherein ends of the proximal and distal members are coated with a sealing material.

9. The device as defined in claim 1, wherein the distal member is made integral with the distal stent and the proximal member is made integral with the proximal stent.

10. The device as defined in claim 1, wherein the proximal member is disposed at an incline with respect to the central axis of the proximal stent so that an open end thereof is directed toward the distal member and the distal member is disposed at an incline with respect to the central axis of the distal member so that an open end of the distal member is directed toward the open end to the proximal member.

11. The device as defined in claim 1, wherein each of the proximal and distal stents are generally cylindrical and have at least one open end and wherein each of the proximal and distal members are generally cylindrical tubular members having open ends.

12. The device as defined in claim 1, wherein each of the proximal and distal stents include retention braces adapted to contact an inner wall of the target lumen.

13. A prosthetic device for bypassing an occlusion in a lumen, the device comprising:
 a generally tubular proximal stent having a central axis and a flow passage defined therethrough and being sized for insertion into the lumen upstream of the occlusion, said proximal stent including a proximal member extending from a sidewall thereof so as to be in flow communication with the flow passage;
 a generally tubular distal stent having a central axis and a flow passage defined therethrough and being sized for insertion into the lumen downstream of the occlusion, said distal stent including a distal member extending from a sidewall thereof so as to be in flow communication with the flow passage of the distal stent; and
 a generally tubular central member having first and second ends and extending between said proximal member and said distal member and being in flow communication therewith so as to provide flow communication between said proximal and said distal stents so as to bypass the occlusion,
 said proximal and distal stents being constructed collapsible and expandable and are and arranged so as to engage walls of the target lumen.

14. The device as defined in claim 13, wherein each of said proximal and distal members extend from said proximal and distal stents to define a generally "Y" configuration.

15. The device as defined in claim 14, wherein each of said proximal and distal stents comprise metal mesh, said first and second ends of said central member being hooded over said proximal member and said distal member, respectively, in such a manner to provide substantially sealed flow communication between said proximal and said distal stents.

16. The device as defined in claim 13, wherein the proximal member is disposed at an incline with respect to the central axis of the proximal stent so that an open end thereof is directed toward the distal member and the distal member is disposed at an incline with respect to the central axis of the distal member so that an open end of the distal member is directed toward the open end to the proximal member.

17. The device as defined in claim 13, wherein each of the proximal and distal stents are generally cylindrical and have at least one open end and wherein each of the proximal and distal members are generally cylindrical tubular members having open ends.

18. A method of installing a device within an occluded lumen so as to bypass the occlusion, the device including a generally tubular first stent having a central axis and a flow passage defined therethrough and being sized for insertion into the occluded lumen, said first stent including a first member extending from a sidewall thereof so as to be in flow communication with the flow passage; a generally tubular second stent having a central axis and a flow passage defined therethrough and being sized for insertion into the occluded lumen, said second stent including a second member extending from a sidewall thereof so as to be in flow communication with the flow passage of the second stent; and a generally tubular central member having first and second ends coupled to said first member and said second member respectively, so as to provide communication between said first and said second stents, the method comprising the steps of:

making a first puncture through a wall of the occluded lumen at a position at one stent entry site one of upstream and downstream of the occlusion;

inserting the first stent in a collapsed state through the first puncture into the occluded lumen;

permitting the first stent to expand so as to engage the interior wall of the occluded lumen;

permitting the first member to extend through the first puncture;

making a second puncture through the wall of the occluded lumen at an another stent entry site so that the occlusion is disposed between the first and second punctures;

inserting the second stent in a collapsed state through the second puncture into the occluded lumen;

permitting the second stent to expand so as to engage the interior wall of the occluded lumen;

permitting the second member to extend through the second puncture; and disposing the central member between the first and second members within subcutaneous tissue and fascia so that fluid may flow through the first stent and first member, through the central member and second member and out through the second stent so as to bypass the occlusion.

19. The method as defined in claim 18, wherein the central member of the device is composed of synthetic material.

20. A method of grafting first and second lumens with a device, the device including a generally tubular first stent having a flow passage defined therethrough and being sized for insertion into the first lumen, said first stent including a first member extending from a sidewall thereof so as to be in flow communication with the flow passage; a generally tubular second stent having a flow passage defined therethrough and being sized for insertion into the second lumen, said second stent including a second member extending from a sidewall thereof so as to be in flow communication with the flow passage of the second stent; and a generally tubular central member having first and second ends coupled to said first member and said second member respectively, so as to be in flow communication with said first and said second stents, the method comprising the steps of:

making a first puncture through a wall of the first lumen;

inserting the first stent in a collapsed state through the first puncture and into the first lumen;

permitting the first stent to expand so as to engage the interior wall of the first lumen;

permitting the first member to extend through the first puncture;

making a second puncture through a wall of the second lumen at another stent entry site;

inserting the second stent in a collapsed state through the second puncture and into the second lumen;

permitting the second stent to expand so as to engage the interior wall of the second lumen; p'permitting the second member to extend through the second puncture; and disposing the central member between the first and second members within subcutaneous tissue and fascia so that fluid may flow through the first stent and first member, through the central member and second member and out through the second stent so as to permit communication between said first and second lumens.

21. A prosthetic device for creating flow communication between first and second lumens, the device comprising:

a generally tubular proximal stent having a central axis and a flow passage defined therethrough and being sized for insertion into the first lumen, said proximal stent including a proximal member extending from a sidewall thereof so as to be in flow communication with the flow passage;

a generally tubular distal stent having a central axis and a flow passage defined therethrough and being sized for insertion into the second lumen, said distal stent including a distal extending from a sidewall thereof so as to be in flow communication with the flow passage of the distal stent; and a generally tubular central member having first and second ends and extending between said proximal member and said distal member and being in flow communication therewith so as to provide flow communication between said proximal and said distal stents and thus said first and second lumens, and said proximal and distal stents being constructed collapsible and expandable and are arranged so as to engage walls of the target lumen.

22. A method of installing a device to bypass an occluded lumen, the device including a generally tubular first stent having a central axis and a flow passage defined therethrough and being sized for insertion into the occluded lumen, said first stent including a first member extending from a sidewall thereof so as to be in flow communication with the flow passage; a generally tubular second stent having a central axis and a flow passage defined therethrough and being sized for insertion into the occluded lumen, said second stent including a second member extending from a sidewall thereof so as to be in flow communication with the flow passage of the second stent; and a generally tubular central member having first and second ends and adapted to extend between said first member and said second member so as to provide communication between said first and said second stents, the method comprising the steps of:

making an incision in skin and fascial layer generally adjacent said occlusion;

tunneling the central member in the skin and fascial layer with the first and second stents affixed thereto so the first and second stents are oriented in a manner such that the occlusion is disposed generally therebetween;

making a first puncture through the occluded lumen wall at a position one of upstream and downstream of the occlusion;

inserting the first stent in a collapsed state through the first puncture into the occluded lumen;

permitting the first stent to expand so as to engage the interior wall of the occluded lumen;

permitting the first member to extend through the first puncture;

making a second puncture through the lumen wall at a position adjacent said first puncture so that the occlusion is disposed between the first and second punctures;

inserting the second stent in a collapsed state through the second puncture into the occluded lumen;

permitting the second stent to expand so as to engage the interior wall of the occluded lumen;

permitting the second member to extend through the second puncture so that fluid may flow through the first stent and first member, through the central member and second member and out through the second stent so as to bypass the occlusion.

* * * * *